United States Patent
Rothenberg et al.

(10) Patent No.: US 10,422,004 B2
(45) Date of Patent: Sep. 24, 2019

(54) DIAGNOSTIC METHOD FOR DISTINGUISHING FORMS OF ESOPHAGEAL EOSINOPHILIA

(71) Applicants: CHILDREN'S HOSPITAL MEDICAL CENTER, Cincinnati, OH (US); THE REGENTS OF THE UNIVERSITY OF CALIFORNIA, Oakland, CA (US)

(72) Inventors: Marc E. Rothenberg, Cincinnati, OH (US); Ting Wen, Cincinnati, OH (US); Seema Aceves, San Diego, CA (US)

(73) Assignees: CHILDREN'S HOSPITAL MEDICAL CENTER, Cincinnati, OH (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 124 days.

(21) Appl. No.: 15/502,273

(22) PCT Filed: Aug. 10, 2015

(86) PCT No.: PCT/US2015/044461
§ 371 (c)(1),
(2) Date: Feb. 7, 2017

(87) PCT Pub. No.: WO2016/023026
PCT Pub. Date: Feb. 11, 2016

(65) Prior Publication Data
US 2017/0233813 A1   Aug. 17, 2017

Related U.S. Application Data

(60) Provisional application No. 62/034,983, filed on Aug. 8, 2014.

(51) Int. Cl.
| | | |
|---|---|---|
| *C12Q 1/68* | (2018.01) | |
| *C12Q 1/6883* | (2018.01) | |
| *G16B 25/00* | (2019.01) | |
| *C08K 5/521* | (2006.01) | |
| *C08K 7/06* | (2006.01) | |
| *G01N 33/68* | (2006.01) | |
| *A61K 31/4439* | (2006.01) | |
| *A61K 31/56* | (2006.01) | |
| *A61K 31/573* | (2006.01) | |
| *A61K 31/58* | (2006.01) | |
| *G16H 10/60* | (2018.01) | |
| *G16H 15/00* | (2018.01) | |
| *G16H 10/20* | (2018.01) | |

(52) U.S. Cl.
CPC ........ *C12Q 1/6883* (2013.01); *A61K 31/4439* (2013.01); *A61K 31/56* (2013.01); *A61K 31/573* (2013.01); *A61K 31/58* (2013.01); *C08K 5/521* (2013.01); *C08K 7/06* (2013.01); *C12Q 1/68* (2013.01); *G01N 33/6872* (2013.01); *G01N 33/6893* (2013.01); *G16B 25/00* (2019.02); *C12Q 2600/112* (2013.01); *C12Q 2600/158* (2013.01); *G01N 2333/705* (2013.01); *G01N 2800/06* (2013.01); *G16H 10/20* (2018.01); *G16H 10/60* (2018.01); *G16H 15/00* (2018.01)

(58) Field of Classification Search
None
See application file for complete search history.

(56) References Cited

U.S. PATENT DOCUMENTS

| | | |
|---|---|---|
| 4,376,110 A | 3/1983 | David et al. |
| 4,675,904 A | 6/1987 | Silverman |
| 5,148,483 A | 9/1992 | Silverman |
| 5,288,644 A | 2/1994 | Beavis et al. |
| 5,445,934 A | 8/1995 | Fodor et al. |
| 5,700,637 A | 12/1997 | Southern |
| 5,744,305 A | 4/1998 | Fodor et al. |
| 5,945,334 A | 8/1999 | Besemer et al. |
| 5,976,081 A | 11/1999 | Silverman |
| 6,054,270 A | 4/2000 | Southern |
| 6,300,063 B1 | 10/2001 | Lipshutz et al. |
| 6,429,027 B1 | 8/2002 | Chee et al. |
| 6,733,977 B2 | 5/2004 | Besemer et al. |
| 6,858,394 B1 | 2/2005 | Chee et al. |
| 7,364,858 B2 | 4/2008 | Barany et al. |
| 9,691,411 B2 | 6/2017 | Scherer et al. |
| 2002/0077825 A1 | 6/2002 | Silverman et al. |
| 2003/0078768 A1 | 4/2003 | Silverman et al. |
| 2003/0167189 A1 | 9/2003 | Lutgen et al. |

(Continued)

FOREIGN PATENT DOCUMENTS

| | | |
|---|---|---|
| EP | 0 619 321 A1 | 10/1994 |
| EP | 0 619 321 B1 | 10/1994 |

(Continued)

OTHER PUBLICATIONS

Strausberg et al, in Microarrays and Cancer Research, 2002, Warrington et al (eds.), Eaton Publishing, Westborough, MA, pp. xi-xvi.*

(Continued)

*Primary Examiner* — James Martinell

(74) *Attorney, Agent, or Firm* — Muriel M. Liberto; Mintz Levin Cohn Ferris Glovsky and Popeo, P.C.

(57) ABSTRACT

The invention provides methods for diagnosing eosinophilic esophagitis in a patient using a biomarker based assay directed to KCNJ2/Kir2.1 and related compositions, kits, and computer program products.

20 Claims, 6 Drawing Sheets

(56) References Cited

U.S. PATENT DOCUMENTS

| | | |
|---|---|---|
| 2007/0233468 A1 | 10/2007 | Ozdas et al. |
| 2007/0233498 A1 | 10/2007 | Silverman et al. |
| 2008/0201280 A1 | 8/2008 | Martin et al. |
| 2010/0262603 A1 | 10/2010 | Odom et al. |
| 2012/0041911 A1 | 2/2012 | Pestian et al. |
| 2012/0283117 A1 | 11/2012 | Rothenberg |
| 2012/0288068 A1 | 11/2012 | Jaiswal et al. |
| 2013/0035961 A1 | 2/2013 | Yegnanarayanan |
| 2016/0180041 A1 | 6/2016 | Pestian et al. |
| 2017/0061073 A1 | 3/2017 | Sadhasivam |

FOREIGN PATENT DOCUMENTS

| | | | |
|---|---|---|---|
| WO | WO-89/10977 | A1 | 11/1989 |
| WO | WO-2010/126867 | A1 | 11/2010 |
| WO | WO-2012/025765 | A1 | 3/2012 |
| WO | WO-2012/177945 | A2 | 12/2012 |
| WO | WO-2012/177945 | A3 | 12/2012 |
| WO | WO-2013/082308 | A1 | 6/2013 |
| WO | WO-2013/126834 | A1 | 8/2013 |
| WO | WO-2013-155010 | A1 | 10/2013 |
| WO | WO-2014-059178 | A1 | 4/2014 |
| WO | WO-2014/190269 | A1 | 11/2014 |
| WO | WO-2015/017731 | A1 | 2/2015 |
| WO | WO-2015/127379 | A1 | 8/2015 |

OTHER PUBLICATIONS

Notterman et al, in Microarrays and Cancer Research, 2002, Warrington et al (eds.), Eaton Publishing, Westborough, MA, pp. 81-111.*

Anderson, B. et al. (Sep. 2011). "Evaluation of a morphine maturation model for the prediction of morphine clearance in children," *Br J Clin Pharmcol* 72(3):518-520; author reply 521-523.

Barratt, D.T. et al. (2012, e-published Apr. 18, 2012). "ABCB1 haplotype and OPRM1 118A > G genotype interaction in methadone maintenance treatment pharmacogenetics," *Pharmgenomics Pers Med* 5:53-62.

Biesiada, J. et al. (Nov. 2014). "Genetic risk signatures of opioid-induced respiratory depression following pediatric tonsillectomy," *Pharmacogenomics* 15(14):1749-1762.

Branford, R. et al. (Oct. 2012, e-published Jul. 27, 2012). "Opioid genetics: the key to personalized pain control?" *Clin Genet* 82(4):301-310.

Clavijo, C.F. et al. (May 2011, e-published Mar. 12, 2011). "A sensitive assay for the quantification of morphine and its active metabolites in human plasma and dried blood spots using high-performance liquid chromatography-tandem mass spectrometry," *Anal Bioanal Chem* 400(3):715-728.

Collins, R.T. et al. (Oct. 2005). "Online selection of discriminative tracking features," *IEEE Trans Patter Anal Mach Intell* 27(10):1631-1643.

Cohen, M. et al. (Aug. 2012). "Pharmacogenetics in perioperative medicine," *Curr Opin Anaesthesiol* 25(4):419-427.

Dellon, E.S. et al. (Dec. 2013, e-published Oct. 22, 2013). "Clinical and endoscopic characteristics do not reliably differentiate PPI-responsive esophageal eosinophilia and eosinophilic esophagitis in patients undergoing upper endoscopy: a prospective cohort study," *Am J Gastroenterol* 108(12):1854-1860.

Dellon, E.S. et al. (May 1, 2014). "Immunohistochemical Evidence of Inflammation Is Similar in Patients with Eosinophilic Esophagitis and PPI-Responsive Esophageal Eosinophilia: A Prospective Cohort Study," *Gastroenterology* 146(5), Supplement 1, p. S-17.

Eissing, T. et al. (Feb. 1, 2012). "Pharmacogenomics of codeine, morphine, and morphine-6-glucuronide: model-based analysis of the influence of CYP2D6 activity, UGT2B7 activity, renal impairment, and CYP3A4 inhibition," *Mol Diagn Ther* 16(1):43-53.

Extended European Search Report dated Nov. 16, 2017, for EP Application No. 15828951.2, filed Aug. 10, 2015, 8 pages.

Fukada, T. et al. (Jul. 2013). "OCT1 genetic variants influence the pharmacokinetics of morphine in children," *Pharmacogenomics* 14(10):1141-1151.

Fukuda, T. et al. (Feb. 2013). *Clinical Pharmacology & Therapeutics* 93:S49.

Guyon, I. et al. (2002). "Gene Selection for Cancer Classification using Support Vector Machines," *Machine Learning* 46:389-422.

Himes, B.E. et al. (May-Jun. 2009, e-published Mar. 4, 2009). "Prediction of chronic obstructive pulmonary disease (COPD) in asthma patients using electronic medical records," *J Am Med Inform Assoc* 16(3):371-379.

International Search Report issued in PCT/US2014/039357 dated Sep. 24, 2014.

International Search Report and Written Opinion issued in PCT/US2014/049301 dated Dec. 8, 2014.

International Search Report issued in PCT/US2015/017134 dated May 6, 2016.

Juffali, W et al. The Winam Project: Neural Data Analysis with Applications to Epilepsyy Biomedical Circuits and Systems Conference (BioCAS), 2010, pp. 45-48.

Kelly, L.E. et al. (May 2012, e-published Apr. 9, 2012). "More codeine fatalities after tonsillectomy in North American children," *Pediatrics* 129(5):e1343-1347.

K R Crews et al: "Clinical Pharmacogenetics Implementation Consortium Guedelines for Cytochrome P450 2D6 Genotype and Codeine Therapy: 2014 Update", Clinical Pharmacology & Therapeutics, vol. 95, No. 4, Jan. 29, 2014 (Jan. 29, 2014), pp. 376-382, XP055185334, ISSN: 0009-9236, DOI: 10.1038/clpt.2013.254 "Therapeutic recommendation" bridging pp. 379 and 380 table 2 "Potential Benefits and Risks for the Patient" on p. 380.

Leschziner, G.D. et al. (Jun. 2007, e-published Sep. 12, 2006). "ABCB1 genotype and PGP expression, function and therapeutic drug response: a critical review and recommendations for future research," *Pharmacogenomics J.* 7(3):154-179.

Meineke, I. et al. (Dec. 2002). "Pharmacokinetic modelling of morphine, morphine-3-glucuronide and morphine-6-glucuronide in plasma and cerebrospinal fluid of neurosurgical patients after short-term infusion of morphine," *Br J Clin Pharmacol* 54(6):592-603.

Mizuno, T. et al. (2013). *Clinical Pharmacology & Therapeutics*, 93:S63.

Mogil, J.S. (Jul. 6, 1999). "The genetic mediation of individual differences in sensitivity to pain and its inhibition," *PNAS USA* 96(14):7744-7751.

Ozdas, Asli, et al. "Investigation of vocal jitter and glottal flow spectrum as possible cues for depression and near-term suicidal risk." IEEE Transactions on Biomedical Engineering 51.9 (2004): 1530-1540.

Park, H.J. et al. (Apr. 2007, e-published Dec. 27, 2006). "Genetic polymorphisms in the ABCB1 gene and the effects of fentanyl in Koreans," *Clin Pharmacol Ther* 81(4):539-546.

Prows, C.A. et al. (May 2014, e-published Nov. 13, 2013). "Codeine-related adverse drug reactions in children following tonsillectomy: a prospective study," *Laryngoscope* 124(5):1242-1250.

Ray, R. et al. (May 31, 2011, e-published May 16, 2011). Human Mu Opioid Receptor (OPRM1 A118G) polymorphism is associated with brain mu-opioid receptor binding potential in smokers, *PNAS USA* 108(22):9268-9273.

Sadhasivam, S. et al. (May 2012, e-published Apr. 23, 2012). "Race and unequal burden of perioperative pain and opioid related adverse effects in children," *Pediatrics* 129(5):832-838.

Sadhasivam, S. et al. (Jul. 2012, e-published Jun. 13, 2012). "Preventing opioid-related deaths in children undergoing surgery," Pain Med 13(7):982-983, author reply 984.

Sadhasivam, S. et al. (Jul.-Aug. 2012). "Morphine clearance in children: does race or genetics matter?" *J Opioid Manag* 8(4):217-226.

Sadhasivam S. et al. (2014). "Genetics of pain perception, COMT and postoperative pain management in children," *The Pharmacogenomics Journal* 15(3):277-284.

Sadhasivam S. et al. (2015). Novel Associations between FAAH Genetic Varients an Postoperative Central Opioid Related Adverse Effects, *The Pharmacogenomics Journal* 15(5):436-442.

(56) References Cited

OTHER PUBLICATIONS

Scherer, Stefan, John Pestian, and Louis-Philippe Morency. "Investigating the speech characteristics of suicidal adolescents." 2013 IEEE International Conference on Acoustics, Speech and Signal Processing. IEEE, 2013.

Tzvetkov, M.V. et al. (Sep. 2013, e-published Jul. 5, 2013). "Morphine is a substrate of the organic cation transporter OCT1 and polymorphisms in OCT1 gene affect morphine pharmacokinetics after codeine administration," *Biochem Pharmacol* 86(5):666-678.

Venek, Verena, et al. "Adolescent suicidal risk assessment in clinician-patient interaction: A study of verbal and acoustic behaviors." Spoken Language Technology Workshop (SLT), 2014 IEEE. IEEE, 2014.

Venkatasubramanian, R. et al. (Jul. 2014). "ABCC3 and OCT1 genotypes influence pharmacokinetics of morphine in children," *Pharmacogenomics* 15(10):1297-1309.

Verspoor, K. et al. (Jun. 15, 2009). "The textual characteristics of traditional and Open Access scientific journals are similar," BMC Bioinformatics 10:183.

Wen, T. et al. (Dec. 2013, e-published Aug. 23, 2013). "Molecular diagnosis of eosinophilic esophagitis by gene expression profiling," Gastroenterology 145(6):1289-1299.

Wen, T. et al. (Jan. 2015, Oct. 19, 2014). "Transcriptome analysis of proton pump inhibitor-responsive esophageal eosinophilia reveals proton pump inhibitor-reversible allergic inflammation," J Allergy Clin Immunol 135(1):187-197.

Xiao-Di Gong et al: "Gene Polymorphisms of OPRM1 A118G and ABCB1 C3435T May Influence Opioid Requirements in Chinese Patients with Cancer Pain", Asian Pacific Journal of Cancer Prevention, vol. 14, No. 5, May 30, 2013 (May 30, 2013), pp. 2937-2943.

Zeng, Q.T. et al. (Jul. 26, 2006). "Extracting principal diagnosis, co-morbidity and smoking status for asthma research: evaluation of a natural language processing system," BMC Med Inform Decis Mark 6:30.

International Search Report dated Nov. 9, 2015 for International Application No. PCT/US2015/044461, filed Aug. 10, 2015, 3 pages.

\* cited by examiner

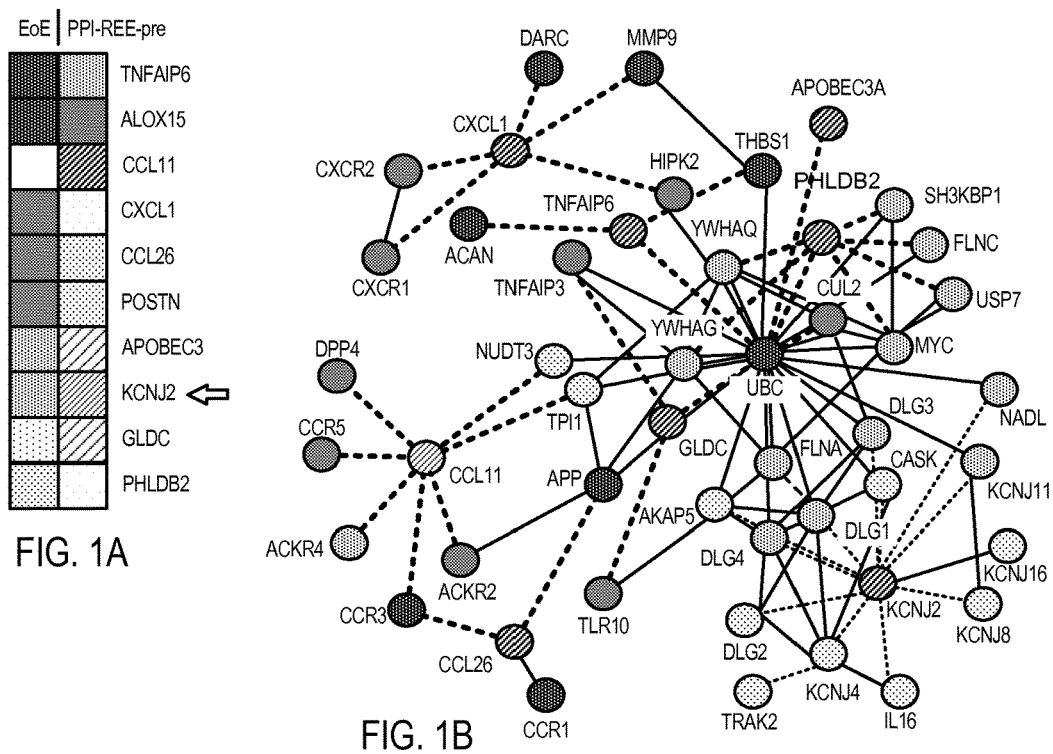
FIG. 1A
FIG. 1B
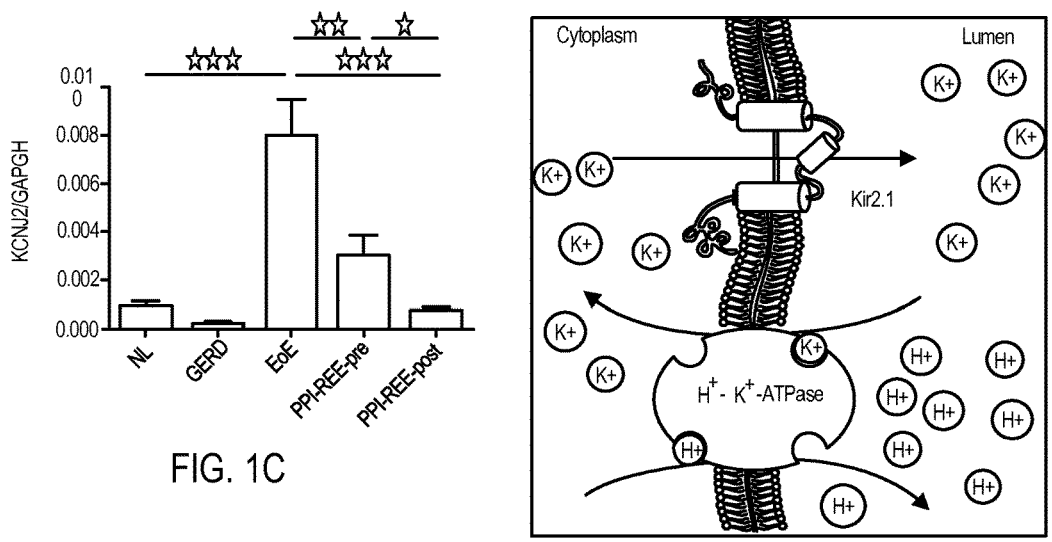
FIG. 1C
FIG. 1D
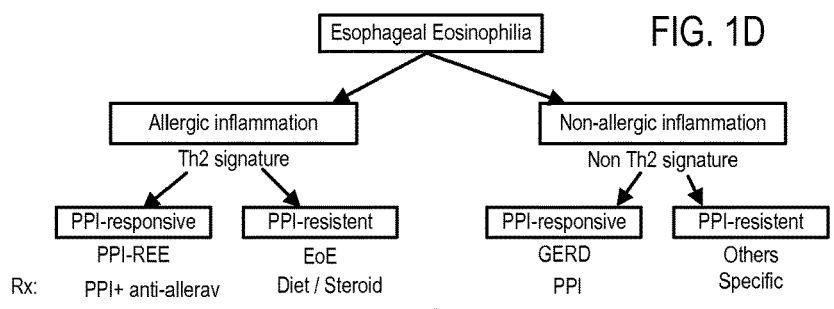
FIG. 1E

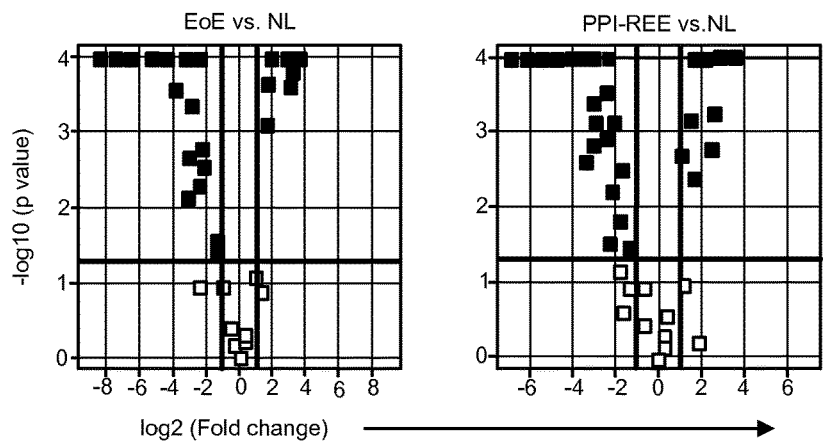

FIG. 2A

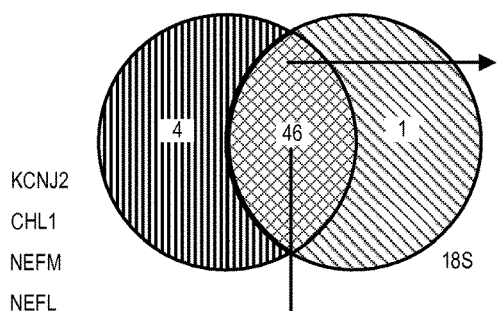

KCNJ2
CHL1
NEFM
NEFL

FIG. 2B

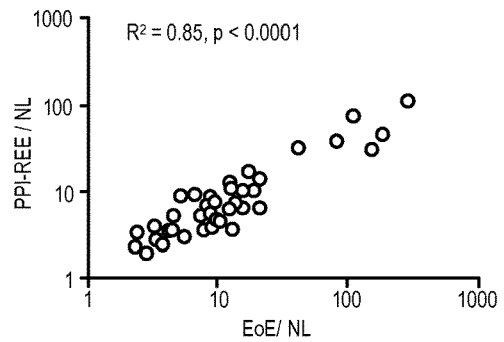

FIG. 2C

Biological processes

1. Immune response
2. Inflammatory response
3. Eosinophil chemotaxis
4. Eosinophil migration
5. Defense response
6. Lipoxin A4 metabolic process
7. Lipoxin biosynthesis process
8. Lipoxin A4 biosynthesis process
9. Response to Wounding
10. Negative regulation of adaptive immunity
11. Cell adhesion
12. Biological adhesion
13. Adaptive immune response
14. Granulocyte chemotaxis

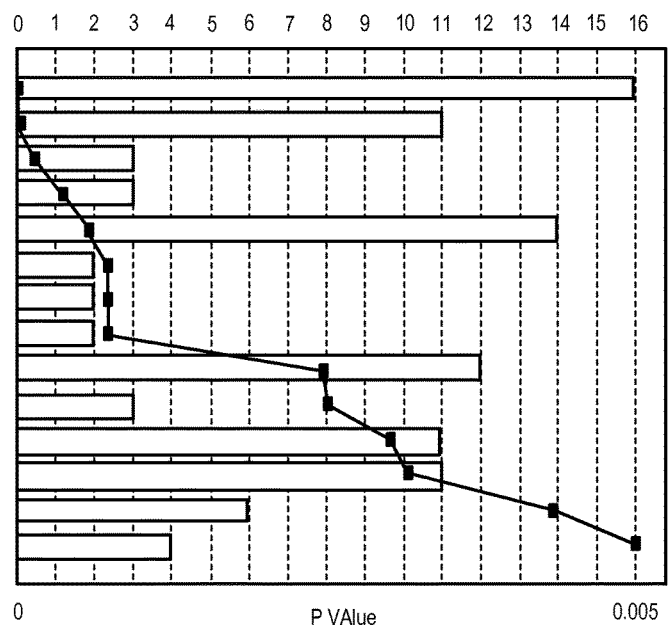

FIG. 2D

DIAGNOSTIC METHOD FOR DISTINGUISHING FORMS OF ESOPHAGEAL EOSINOPHILIA

CROSS-REFERENCE TO RELATED APPLICATIONS

This application is a national stage entry, filed under 35 U.S.C. § 371, of International Application No. PCT/US2015/044461, filed on Aug. 10, 2015, which claims the benefit of and priority to U.S. Provisional Patent Application No. 62/034,983, filed Aug. 8, 2014, the entire contents of which are hereby incorporated herein by reference in their entirety and for all purposes.

STATEMENT REGARDING FEDERALLY-SPONSORED RESEARCH

This invention was made with government support under DK078392, AI083450, DK076893, AI070235, and AI045898 awarded by the National Institutes of Health. The government has certain rights in the invention.

FIELD OF THE INVENTION

The invention disclosed herein generally relates to diagnostic methods and compositions for esophageal eosinophilia.

BACKGROUND

Esophageal eosinophilia occurs in patients with a number of disorders, including gastroesophageal reflux disease (GERD), Crohn disease, celiac disease, and eosinophilic esophagitis (EoE), a clinicopathologic chronic upper gastrointestinal tract disorder defined by esophageal dysfunction and eosinophil infiltration of 15 or more eosinophils per high-power field (hpf). Translational research in the past 10 years has uncovered a food allergen-driven, TH2 cell immune-mediated disease pathogenesis. Because GERD can also elicit esophageal eosinophilia, a consensus recommendation for the diagnosis of EoE requires a proton pump inhibitor (PPI) trial to exclude the possibility of acid-induced esophageal eosinophilia.

Although EoE is defined by a failed PPI trial, another form of esophageal eosinophilia that is frequently observed features tissue eosinophil levels as high as those in patients with EoE (in contrast to patients with GERD), diffuse infiltration along the esophageal length, and clinical characteristics representative of EoE, but PPI monotherapy is effective in reversing both histologic and clinical abnormalities. A number of explanations have been proposed, including (1) blockade of GERD-associated inflammation through the inhibition of acid by PPI; (2) the anti-inflammatory effects of PPI, such as inhibition of eotaxin-3 and signal transducer and activator of transcription; and (3) the interaction of acid and food allergens. Because of the lack of a clear understanding of the natural history and pathogenesis, this enigmatic condition is currently termed PPI-responsive esophageal eosinophilia (PPI-REE).

The frequency of PPI-REE among all patients with esophageal eosinophilia (>15 eosinophils/hpf) is substantial, ranging from 10% to 50%. Defining the underlying mechanisms of this inflammation in patients with PPI-REE will help to guide appropriate therapeutic strategies. However, to date, there have been no molecular, cellular, endoscopic, or clinical markers or pH test results that clearly distinguish these entities from one another. EoE is treated with topical corticosteroids and/or dietary elimination, whereas PPI-REE is treated, at least transiently, with acid suppression. Currently, it remains to be determined whether these 2 entities involve the same or different molecular pathogeneses. An understanding of their molecular similarities and differences would provide diagnostic and therapeutic clarity for practitioners and patients because both patients with PPI-REE and those with EoE are clinically similar in terms of clinical symptoms, endoscopic findings, male predominance, and high rate of atopy.

SUMMARY OF THE INVENTION

The invention is based, in part, on the inventors' discovery of a biomarker for eosinophilic esophagitis (EoE), and specifically one that can distinguish EoE from PPI-responsive esophageal eosinophilia (PPI-REE). At the time of the invention these two diseases, which are treated by different and non-complementary therapies, were differentiated by subjecting a patient suspecting of having EoE to a proton pump inhibitor (PPI) trial. Since patients having EoE do not respond to PPI therapy, a diagnosis of EoE could be made if the patient failed the trial. The present invention improves care for EoE patients by providing methods for making an accurate diagnosis of EoE without the need for a PPI trial.

The invention provides methods for diagnosing EoE in a patient in need of such diagnosis, the method comprising receiving or obtaining an esophageal biopsy sample from the patient; determining the expression level of the KCNJ2/Kir2.1 gene or gene product in the esophageal biopsy sample; determining whether the expression level of the KCNJ2/Kir2.1 gene or gene product in the esophageal biopsy sample is above or below a threshold level; and diagnosing the patient as having eosinophilic esophagitis if the expression level of the KCNJ2/Kir2.1 gene or gene product is above the threshold level. The methods described herein do not require a proton pump inhibitor (PPI) trial, and the patient undergoing diagnosis for EoE according to the present methods is preferably one who has not been previously treated with a proton pump inhibitor.

In some embodiments, the threshold level is relative to a reference expression level of the KCNJ2/Kir2.1 gene or gene product, hereinafter referred to as "the reference". The reference is a value representing the expression level of the KCNJ2/Kir2.1 gene or gene product in normal esophageal tissue. In one embodiment, the reference expression level is a mean of a plurality of KCNJ2/Kir2.1 gene or gene product expression levels from normal esophageal tissue. In this context, the term "normal" in reference to esophageal tissue is defined according to standard clinical practice. For example, normal tissue may be defined as having each of the following characteristics: normal endoscopic results, normal pathology with 0 eosinophils/high power field, and no known history of eosinophilic esophagitis in the patient from whom the sample was obtained. In one embodiment, the reference is pre-determined.

In one embodiment, the threshold level is from 1.5 to 3-fold greater than the reference. In one embodiment, the threshold level is 2 or 3-fold greater than the reference. In another embodiment, the threshold level is 1.5-fold greater than the reference.

The expression levels of the KCNJ2/Kir2.1 gene or gene product may be determined by methods for quantifying gene expression and protein expression known in the art. For example, in one embodiment gene expression is determined using a quantitative polymerase chain reaction (PCR)-based method. Such methods may comprise a number of sample processing and detection steps, e.g., steps for extracting RNA from the biological sample (e.g., the patient biopsy sample and/or the control biopsy sample), converting the RNA to cDNA, converting the cDNA into cRNA, labeling the KCNJ2/Kir2.1 cDNA or cRNA with a detectable marker, and measuring the amount of the detectable marker in the sample. Methods for quantifying protein expression may also comprise sample processing and detection steps, e.g., steps for extracting protein from the biological sample (e.g., the patient biopsy sample), labeling the KCNJ2/Kir2.1 protein with a detectable marker, and measuring the amount of the detectable marker in the sample. In one embodiment, the expression levels of the KCNJ2/Kir2.1 gene product are determined using an immunofluorescence based method, for example confocal microscopy. In accordance with any of these methods, the expression levels of the KCNJ2/Kir2.1 gene or gene product may be normalized to an internal or external control, or both, in accordance with standard practice for quantitating gene and protein expression.

The invention also provides a computer program product, stored on a non-transitory computer readable medium, containing executable instructions that when executed cause a processor to perform operations comprising receiving the expression level of a KCNJ2/Kir2.1 gene or gene product in an esophageal biopsy sample obtained from a patient, and optionally, receiving a reference expression level of the KCNJ2/Kir2.1 gene or gene product from normal esophageal tissue; receiving or calculating a threshold value; comparing the KCNJ2/Kir2.1 gene or gene product expression level in the esophageal biopsy sample with the threshold value; determining whether the KCNJ2/Kir2.1 gene or gene product expression level in the esophageal biopsy sample is above or below the threshold value; an outputting an indication of whether the KCNJ2/Kir2.1 gene or gene product expression level in the esophageal biopsy sample is above or below the threshold value.

In one embodiment, the indication comprises or is comprised in a patient-specific report. In one embodiment, the report comprises a suggested diagnosis of eosinophilic esophagitis if the KCNJ2/Kir2.1 gene or gene product expression level in the esophageal biopsy sample is above the threshold value, or a suggested diagnosis of PPI-REE if the KCNJ2/Kir2.1 gene or gene product expression level in the esophageal biopsy sample is below the threshold value. In one embodiment, the report further comprises a treatment recommendation. In one embodiment, the computer program product further comprises executable instructions for querying a database of electronic health records. In one embodiment, the expression level of the KCNJ2/Kir2.1 gene or gene product is received directly from equipment used in determining the expression level.

BRIEF DESCRIPTION OF THE DRAWINGS

FIG. 1A-E. Gene cluster differentially expressed between the EoE and PPI-REE-pre groups. A, List of 10 EoE genes (within the EDP) whose expression is significantly different between the EoE and PPI-REE-pre groups (2-tailed Student t test, $P<0.05$, fold change $>2.0$, n 5 33 for the EoE group and n 5 28 for the PPI-REE-pre group). Arrowhead, KCNJ2. B, A predicative protein-protein interaction derived from the pathway analysis of the 10 significant genes, EoE versus PPI-REE-pre groups. C, with a false discovery correction filter (Westfall-Young permutation), KCNJ2 (Kir2.1) is the only significant gene within the scope of the EDP (EoE vs PPI-REE-pre groups, corrected P 5 0.04). *$P<0.05$, $P<0.01$, and *$P<0.001$ (mean 6 SEM). GAPDH, Glyceraldehyde-3-phosphate dehydrogenase. D, A hypothetical illustration suggesting the interaction of the proton pump (H1-K1-ATPase) and Kir2.1 in the gastrointestinal mucosa. E, A proposed schematic illustration of the classification and treatment of esophageal eosinophilia. Scatterplot data were presented as mean 6 SEM.

FIG. 2A-D. PPI-REE exhibits a continuum of EoE's allergic inflammation signatures. A and B, Within the scope of EDP F59, bioinformatics comparison ($P<0.05$, fold change $>2.0$, 2-tailed unpaired t test) yielded 50 and 47 significant genes between the EoE and NL groups and the PPI-REE-pre and NL groups, respectively. A pair of volcano plots (log 2 fold change as x-axis and 2 log 10 P value as y-axis) demonstrates the similarity of bidirectional dysregulation in the EoE and PPI-REE groups when compared with the NL reference group. C, A dysregulation (based on fold change over NLs) linear correlation analysis between the EoE (EoE/NL) and PPI-REE (PPI-REE/NL) groups was shown on the basis of the 46 overlapping EoE genes dysregulated in both the EoE and PPI-REE groups. D, On the basis of these 46 common genes, a gene ontology analysis focusing on biological function was performed with the number of genes and corresponding P values shown, revealing a pathologic basis for an adaptive TH2 allergic inflammation ($P<0.05$, Bonferroni correction).

DETAILED DESCRIPTION OF THE INVENTION

Figure 3A:
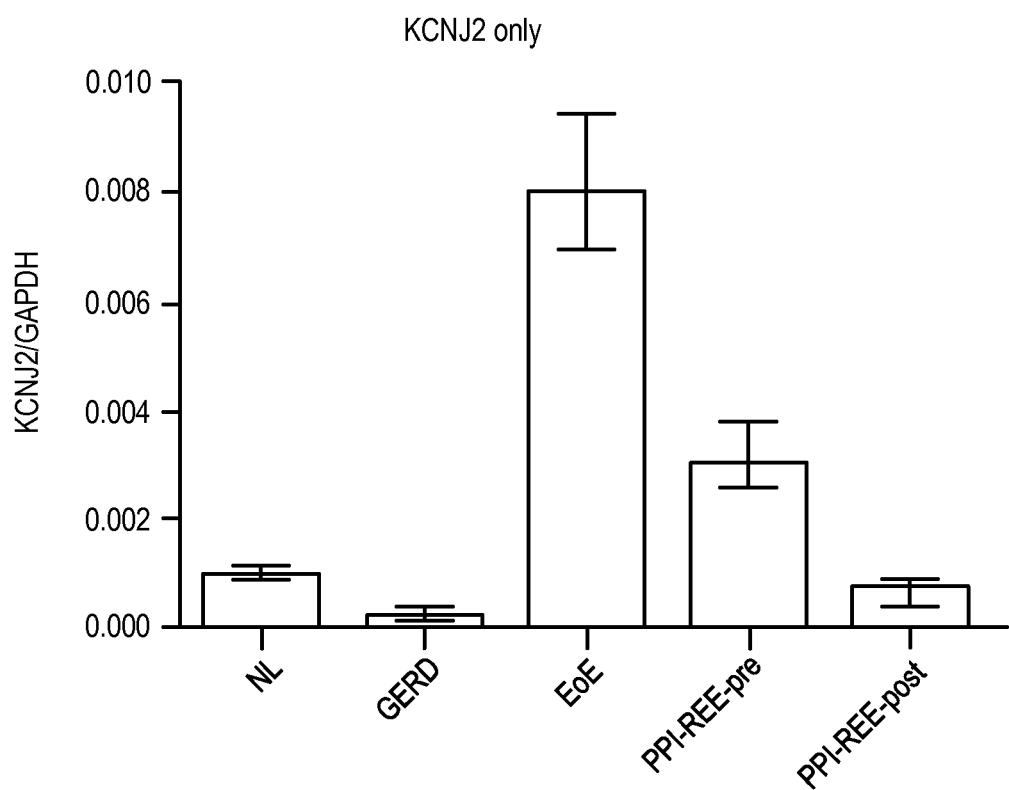
FIG. 3A-3B: A, Gene expression analysis of KCNJ2 in esophageal biopsy tissue using qPCR, number of samples shown in parenthesis, NL (16), GERD (13), EoE (33,) PPI-REE-pre (28), PPI-REE-post (24), error bars indicate SEM; B, ROC of KCNJ2 only:ROC curve showing AUC of 0.73.

The invention provides methods for diagnosing EoE in a patient in need of such diagnosis, and related compositions, kits, and computer program products. Since EoE and PPI-REE before PPI treatment (PPI-REE-pre) are clinically and histologically indistinguishable, while at the same time differing dramatically in their response to PPI treatment, the ability to distinguish between these two conditions before subjecting patients to an ultimately ineffective course of PPI treatment represents a significant advance for patient care and is expected to result in shortened time to correct diagnosis and the initiation of effective treatment. The present methods are based, in part, upon work by the inventors demonstrating that PPI-REE-pre and EoE have different gene expression signatures and that the expression levels of at least one gene, KCNJ2/Kir2.1, can be used to distinguish these conditions.

As used herein, the term "expression level of a KCNJ2/Kir2.1 gene" refers to mRNA expression, i.e., KCNJ2/Kir2.1 mRNA, and the term "expression level of a KCNJ2/Kir2.1 gene product" refers to protein expression, i.e., KCNJ2/Kir2.1 protein.

The expression level of the KCNJ2/Kir2.1 gene may be measured, for example, using a quantitative PCR based method, or by a method comprising gel electrophoresis of cellular RNA, optionally enriched for mRNA, or converted to cDNA, followed by capillary transfer of the RNA or cDNA from the gel to a membrane and detection of specific nucleic acids with a probe according to standard protocols, for example, using the techniques referred to in the art as Northern and Southern blotting. Other techniques may also be used, including for example so-called reverse Northern blotting in which the probe is RNA extracted from the tissue and labelled, e.g., radioactively labelled.

The expression level of the KCNJ2/Kir2.1 gene product may be measured using any suitable means for measuring protein expression in a tissue sample, for example, using an immunostaining-based method, an antibody-based method, a method comprising mass spectrophotometry, or any combination thereof. For example, protein expression may be measured using a technique referred to as Western blotting, which is a protein immunoblotting technique. This technique comprises steps of separating a sample of proteins from a tissue using gel electrophoresis, transferring the separated proteins to a membrane, and using protein or peptide specific antibodies to detect a protein or peptide of interest. Protein expression may also be detected using an immunoassay such as ELISA (enzyme-linked immunosorbent assay). ELISA utilizes a solid-phase immunoassay to detect the presence of a protein in a sample.

In one embodiment, KCNJ2 protein expression is detected and quantitated using and ELISA-based assay performed on a sample of biopsy protein lysate from a patient. In one embodiment, the amount of KCNJ2 protein in the biopsy is normalized to the weight of the biopsy sample.

As used herein, the terms "KCNJ2" and "Kir2.1" both refer to the Potassium Channel, Inwardly Rectifying Subfamily J, Member 2, which may also be referred to in the literature by a number of other aliases including Potassium Inwardly-Rectifying Channel, Subfamily J, Member 2, Cardiac Inward Rectifier Potassium Channel, IRK1, IRK-1, HIRK1, HHIRK1, and ATFB9. Potassium channels are present in most mammalian cells, where they participate in a wide range of physiologic responses. The protein encoded by this gene is an integral membrane protein and inward-rectifier type potassium channel and is believed to play a role in establishing action potential waveform and excitability of neuronal and muscle tissues. Inward rectifier potassium channels are characterized in general by a greater tendency to allow potassium to flow into the cell rather than out of it. Their voltage dependence is regulated by the concentration of extracellular potassium; as external potassium is raised, the voltage range of the channel opening shifts to more positive voltages. The inward rectification is mainly due to the blockage of outward current by internal magnesium and can be blocked by extracellular barium or cesium. RefSeq DNA sequences for KCNJ2 include the following: NC_000017.11, NT_010783.16, and NC_018928.2.

The KCNJ2 gene encodes a protein of 427 amino acids having a mass of 48288 Da (48.3 kDa). The Protein Symbol is P63252-KCNJ2_HUMAN, its recommended name is Inward rectifier potassium channel 2; its Protein Accession No. is P63252; and secondary accession numbers include O15110 and P48049.

In one embodiment, the methods of the invention comprise determining whether the expression level of the KCNJ2/Kir2.1 gene or gene product in the esophageal biopsy sample is above or below a threshold level. The threshold level is determined using a receiver operating characteristic (ROC) curve. The curve is created by plotting the true positive rate (TPR) against the false positive rate (FPR) at various threshold settings. The true-positive rate is also known as sensitivity. The false-positive rate can be calculated as (1-specificity). The ROC curve is thus the sensitivity as a function of specificity. For example, ROC analysis indicates a threshold level of about 1400 fluorescent units in experiments where confocal microscopy was used to analyze KCNJ2/Kir2.1 protein from esophageal biopsy samples, as shown in Table 1 below.

TABLE 1

Data for ROC curve of KCNJ2/Kir2.1 protein expression

| | Sensitivity % | 95% Cl | Specificity % | 95% Cl | Likelihood ratio |
|---|---|---|---|---|---|
| <635.5 | 12.50 | 0.3160% to 52.65% | 100.0 | 63.06% to 100.0% | |
| <734.0 | 25.00 | 3.185% to 65.09% | 100.0 | 63.06% to 100.0% | |
| <893.5 | 37.50 | 8.523% to 75.51% | 100.0 | 63.06% to 100.0% | |
| <1023 | 50.00 | 15.70% to 84.30% | 100.0 | 63.06% to 100.0% | |
| <1102 | 62.50 | 24.49% to 91.48% | 100.0 | 63.06% to 100.0% | |
| <1202 | 75.00 | 34.91% to 96.81% | 100.0 | 63.06% to 100.0% | |
| <1294 | 75.00 | 34.91% to 96.81% | 87.50 | 47.35% to 99.68% | 6.00 |
| <1352 | 87.50 | 47.35% to 99.68% | 87.50 | 47.35% to 99.68% | 7.00 |
| <1411 | 100.0 | 63.06% to 100.0% | 87.50 | 47.35% to 99.68% | 8.00 |
| <1467 | 100.0 | 63.06% to 100.0% | 75.00 | 34.91% to 96.81% | 4.00 |
| <1511 | 100.0 | 63.06% to 100.0% | 62.50 | 24.49% to 91.48% | 2.67 |
| <1582 | 100.0 | 63.06% to 100.0% | 50.00 | 15.70% to 84.30% | 2.00 |
| <1678 | 100.0 | 63.06% to 100.0% | 37.50 | 8.523% to 75.51% | 1.60 |
| <1804 | 100.0 | 63.06% to 100.0% | 25.00 | 3.185% to 65.09% | 1.33 |
| <1984 | 100.0 | 63.06% to 100.0% | 12.50 | 0.3160% to 52.65% | 1.14 |

Eosinophilic esophagitis (EoE) is considered to be a chronic immune system disease. Although it was identified only during the last twenty years, it is now considered a major cause of digestive system (gastrointestinal) illness. In EoE, eosinophils (a type of white blood cell) build up in the lining of the esophagus. This buildup, which may be a reaction to foods, allergens or acid reflux, can inflame and/or injure the esophageal tissue. Damaged esophageal tissue can lead to difficulty swallowing or lead to other complications. Symptoms include difficulty swallowing (dysphagia), food impaction, chest pain that is often centrally located and does not respond to antacids, persistent heartburn, upper abdominal pain, lack of response to gastroesophageal reflux disease (GERD) medication, and backflow of undigested food (regurgitation).

Current clinical standards for diagnosis of EoE include (i) endoscopy to inspect the lining of the esophagus for inflammation and swelling, horizontal rings, vertical furrows, narrowing (strictures) and white spots; (ii) biopsy of esophageal tissue with one biopsy showing more than 15 eosinophils per high power field in patients using a proton pump inhibitor (PPI) for approximately 8 weeks.

Treatment for EoE that is not responsive to PPIs includes an orally administered topical steroid, such as fluticasone or budesonide. Where topical steroids prove ineffective, prednisone may be prescribed.

While the term "subject" includes any mammal, e.g., a human, primate, vertebrate, bird, mouse, rat, fowl, dog, cat, cow, horse, goat, camel, sheep or a pig, preferably the mammal is a human, and therefore the subject is preferably a human. The term "patient" as used herein refers to a human subject.

A subject or patient "in need of" diagnosis or treatment according to the methods described herein is one presenting with one or more the following symptoms of EoE: difficulty swallowing (dysphagia), food impaction, chest pain that is often centrally located and does not respond to antacids, persistent heartburn, upper abdominal pain, lack of response to gastroesophageal reflux disease (GERD) medication, and backflow of undigested food (regurgitation).

In certain embodiments, the human subject is selected from an adult subject, an adult male subject, a pediatric subject, or an elderly (geriatric) subject, as those terms are understood in the medical arts. In certain embodiments, the subject is further defined according to the subject's ethnicity. For example, in one embodiment the subject self-identifies or is genetically determined to be a member of an ethnic group selected from African, North African, Southern African, European, Western European, Northern European, Asian, Japanese, Han Chinese, and Korean. In one embodiment, the subject is of European ethnicity. In this context, the terms ethnicity and ancestry are used interchangeably.

As used herein, "treatment", "treating" or "treat" describes the management and care of a patient for the purpose of combating a disease, condition, or disorder and includes the administration of a therapeutic composition or compositions to alleviate the symptoms or complications of a disease, condition or disorder, or to eliminate the disease, condition or disorder.

As used herein, the term "sample" encompasses a sample obtained from a subject or patient. Generally, a sample can be of any biological tissue or fluid. Such samples include, but are not limited to, sputum, saliva, buccal sample, oral sample, blood, serum, mucus, plasma, urine, blood cells (e.g., white cells), circulating cells (e.g. stem cells or endothelial cells in the blood), tissue, core or fine needle biopsy samples, cell-containing body fluids, free floating nucleic acids, urine, stool, peritoneal fluid, and pleural fluid, liquor cerebrospinalis, tear fluid, or cells therefrom. Samples can also include sections of tissues such as frozen or fixed sections taken for histological purposes or micro-dissected cells or extracellular parts thereof. A sample to be analyzed can be tissue material from a tissue biopsy obtained by aspiration or punch, excision or by any other surgical method leading to biopsy or resected cellular material. Such a sample can comprise cells obtained from a subject or patient. In some embodiments, the sample is a body fluid that include, for example, blood fluids, serum, mucus, plasma, lymph, ascitic fluids, gynecological fluids, or urine but not limited to these fluids. In some embodiments, the sample can be a non-invasive sample, such as, for example, a saline swish, a buccal scrape, a buccal swab, and the like.

As used herein, the term "assessing" includes any form of measurement, and includes determining if an element is present or not. The terms "determining," "measuring," "evaluating," "assessing" and "assaying" can be used interchangeably and can include quantitative and/or qualitative determinations.

As used herein, the term "expression levels" refers, for example, to a determined level of gene (mRNA) or protein expression. The expression levels may be normalized to a reference (e.g. a constitutively expressed "housekeeping" gene, an inversely regulated genes, or the same gene in normal tissues), or to a computed average expression value (e.g. in DNA-chip analyses).

Certain embodiments of the invention include using quantification data from a gene-expression analysis and/or from protein expression analysis from a sample, e.g. a tissue biopsy sample, preferably an esophageal tissue biopsy sample.

Embodiments of the invention include not only methods of conducting and interpreting the diagnostic tests described herein, but also include reagents, kits, assays, and the like, for conducting the tests.

The methods described here may also include generating and outputting a patient-specific report identifying the patient according to the patient's diagnosis, providing an assessment of that diagnosis, and including proposed therapies and/or interventions tailored to the patient's diagnosis.

EXAMPLES

The following non-limiting examples are provided to further illustrate embodiments of the invention disclosed herein. It will be appreciated by those of skill in the art that the techniques disclosed in the examples that follow represent approaches that have been found to function well in the practice of the invention and thus can be considered to constitute examples of modes for its practice. However, those of skill in the art will, in light of the present disclosure, appreciate that many changes can be made in the specific embodiments that are disclosed and still obtain a like or similar result without departing from the spirit and scope of the invention.

Example 1

Distinguishing Untreated PPI-REE and EoE

Substantial progress has been made with regard to the molecular cause of EoE by using whole-genome transcript expression profiling of esophageal tissue. Recently, we identified a molecular EoE diagnostic panel (EDP) that is composed of 94 EoE genes and distinguishes patients with EoE from control subjects without esophagitis or with GERD. Although the EDP has excellent accuracy (>96% sensitivity and specificity), it has not been previously applied to patients with PPI-REE.

In light of these points, a retrospective study with archived tissues was conducted to answer the following crucial questions: (1) Does PPI-REE possess a typical EoE molecular signature that is characteristic of allergic inflammation, as defined by the EDP, or a unique gene expression profile? (2) Does remission induced by PPI monotherapy lead to transcript signature reversal? (3) Does the gene dysregulation in patients with PPI-REE correlate with eosinophilia at the molecular level, similar to that in EoE? (4) Are there gene expression profiles that can differentiate patients with PPI-REE from those with EoE before a therapeutic PPI trial that are a priori?

Our study, further details of which can be found in U.S. Provisional Application Ser. No. 62/034,983, filed Aug. 8, 2014, incorporated herein by reference in its entirety, and later published as *J. Allergy Clin Immunol* 2015 135:187-97, demonstrated that PPI-REE before PPI therapy has a molecular signature that is similar to that of EoE and that this pre-therapy PPI-REE gene expression profile is reversed in parallel with PPI-induced remission. Finally, and of particular clinical relevance, we identified a preliminary cluster of genes that is predictive for PPI-REE before intervention. This is discussed in detail below.

Considering that EoE and PPI-REE before PPI treatment (PPI-REE-pre) are clinically and histologically indistinguishable but different in their therapeutic response to PPI treatment, a molecular approach to identify PPI-REE before pharmaceutical intervention would be a transformative advance for patient care.

To molecularly differentiate these diseases, we collectively compared the EDP molecular signature of the EoE and PPI-REE-pre cohorts at the individual gene level. The EDP molecular signature refers to the EoE transcriptome determined, as reported previously (Wen T, Stucke E M, Grotjan T M, Kemme K A, Abonia J P, Putnam P E, et al. Molecular diagnosis of eosinophilic esophagitis by gene expression profiling. *Gastroenterology* 2013; 145:1289-99), by using the EDP from RNA extracted from 60- to 80-mm tissue sections from formalin-fixed, paraffin-embedded (FFPE) blocks taken from study subjects (see below for subject selection). Briefly, 500 to 1000 ng of RNA was reverse transcribed to cDNA and subjected to EDP amplification by using the ABI 7900HT qPCR system (Applied Biosystems, Foster City, Calif.). The data were then imported into GeneSpring (GX 12.5) software for implementation of the dual algorithm, namely cluster analysis and EoE score calculation. To compensate for the long archiving time for some of the FFPE samples, a 50% call rate filter was applied to the 77 definitive diagnostic genes11 to focus on informative genes, resulting in a cluster of 59 genes (F59) that formed the basis of all of the following analyses.

We identified a cluster of 10 genes whose expression was significantly different in the PPI-REE-pre group compared with the EoE group (P<0.05, fold change >2.0; FIG. 1A). On the basis of these 10 differentially expressed genes, a proposed protein-protein interaction network highlighted the potential involvement of chemotaxis systems, ion channel activities, and the ubiquitin/proteasome system in differentiating molecular pathogenesis between the EoE and PPI-REE-pre groups (FIG. 1B). With a more stringent false detection filter (Westfall-Young) applied, KCNJ2 (potassium inwardly-rectifying channel, subfamily J, member 2/Kir2.1) became the only gene with significant differential expression (P<0.01, false-corrected P 5 0.04; FIG. 1C). For diagnostic merit, using KCNJ2 resulted in 72% sensitivity and 72% specificity to predict PPI-REE-pre versus EoE. KCNJ2 encodes the potassium channel Kir2.1, which is abundant in gastrointestinal mucosa and colocalizes with the Hl-K1-ATPase/proton pump; therefore, we propose a potential interaction between this potassium channel and proton pump in the upper gastrointestinal epithelium (FIG. 1D).

It is notable that KCNJ2 was among the 4 genes that are specifically differentially expressed in the EoE group compared with the NL group but not in the PPI-REE group versus the NL group (FIG. 2B) and that it is expressed in the esophagus.

We also performed additional analyses to address whether the transcriptomes of patients with EoE and those with PPI-REE are similar at the single-gene level. First, when compared with the NL reference, the EoE and PPI-REE-pre groups yielded a similar number of significant genes with comparable bidirectional distribution patterns, as shown by the volcano plots of fold change and P value (FIG. 2A). A large percentage of the significant genes (46 genes vs the NL group) overlapped between the EoE and PPI-REE-pre groups (FIG. 2B). There was a high correlation of the expression levels of these 46 common genes between patients with EoE and those with PPI-REE (R2 5 0.85, P<0.0001; FIG. 2C). Moreover, an ontologic analysis on biological functions on these 46 common genes revealed an overall image of TH2 allergic inflammation with high significance (FIG. 2D), indicating a shared allergic inflammatory response between patients with EoE and those with PPI-REE.

Our results suggest that PPI-REE is allergic in nature and that its clinical management might be more similar to EoE rather than GERD. Moreover, being able to differentiate patients with EoE and those with PPI-REE before the PPI trial would be a meaningful advance for patients, possibly shortening time to diagnosis and effective treatment. Having predictor genes makes untreated PPI-REE and EoE potentially distinguishable before PPI treatment, leading to a new conceptual classification of esophageal eosinophilia. Moreover, being able to predict the PPI response might significantly enhance the patient's quality of life and will likely reduce medical costs because of the distinct therapies for PPI-REE and EoE.

We initially identified a cluster of 10 genes capable of differentiating EoE and PPI-REE-pre. After a subsequent false-detection filter, differential KCNJ2 expression between the EoE and PPI-REE-pre groups remained significant. Interestingly, Kir2.1 has a unique biological significance because this potassium channel was found to be coupled to the proton pump in the gastrointestinal epithelium. Moreover, Kir2.1 conductance property is subjected to pH change and is involved in acid secretion from parietal cells. Kir2.1 ensures that the potassium ion produced by the proton pump as a byproduct can be readily removed from the intracellular space. Therefore, a lower KCNJ2 expression level, as in the case of PPI-REE, could result in lower efficiency of the proton pump and help explain the efficacy of PPI.

Subject Selection and Study Design

Previously collected and archived paraffin-embedded samples from patients with PPI-REE, EoE, or GERD and healthy control subjects were obtained from 5 US institutions: University of California, San Diego/Rady Children's Hospital, San Diego; University of North Carolina—Chapel Hill; Walter Reed National Military Medical Center; Cincinnati Children's Hospital Medical Center (CCHMC); and Children's Hospital Colorado (see Table E1 in this article's Online Repository at www.jacionline.org). The inclusion criteria for patients with PPI-REE, as well as for patients with EoE, patients with GERD, and healthy control subjects (NL group), were standardized before the experiments and data analysis. Experts from each institution agreed on the definition and inclusion criteria and were directly involved in screening of patients with PPI-REE in their sites, identifying those with samples available before and after PPI therapy, as well as determining samples from patients with EoE, patients with GERD, and healthy control subjects. Specifically, control subjects were defined by normal endoscopic results, normal pathology with 0 eosinophils/hpf, and no known history of EoE. Patients with GERD were defined by clinical symptoms consistent with reflux (eg, heartburn and regurgitation), less than 15 peak eosinophils/hpf on biopsy, and no previous EoE history. A portion of the patients with GERD from CCHMC were confirmed to have reflux by means of concurrent pH/impedance testing.

Patients with EoE were defined as having symptomatic esophageal dysfunction and 15 or more peak esophageal eosinophils/hpf, even after an 8- to 12-week PPI trial, as per consensus guidelines. Patients with PPI-REE were defined as having symptoms consistent with esophageal dysfunction and initial esophageal eosinophilia of 15 or more eosinophils/hpf on index endoscopy that resolved (<15 eosinophils/hpf) after an 8-week course of PPI therapy (20-40 mg of available agents twice daily for adults or 10-30 mg of available agents twice daily for pediatric subjects). All patients with PPI-REE exhibited symptomatic (improvement of symptoms by means of self-report at the time of the repeat endoscopy) and endoscopic improvements after monotherapy with PPI. Both adult (>18 years) and pediatric (<18 years) subjects were included in the study. All secondary causes of gastrointestinal tract eosinophilia, including concomitant eosinophilic gastroenteritis, were excluded before confirming the diagnosis of EoE. Atopy was defined by clinical diagnosis and a documented history of food allergies determined by means of either clinical reactions or skin testing. This study was approved by the institutional review boards of the participating institutions.

Statistical and Bioinformatics Analysis

[51] The transcriptomes of the entire cohort of 114 samples (from 96 independent subjects) were compared by using clustering (the signature analysis), EoE score calculation, ANOVA, and principal component analysis (PCA). Most of our algorithm tools were previously reported.11 Briefly, an EoE score (F59) was derived from entities that passed a greater than 50% call rate filter, resulting in 59 of the 77 diagnostic genes of the EDP. With the individual EoE scores (F59) from the 5 subject groups (healthy control subjects and patients with GERD, EoE, PPI-REE before PPI treatment [PPI-REE-pre], or PPI-REE after PPI treatment [PPI-RRE-post]), 1-way ANOVA with the Bonferroni multiple comparison posttest was used to identify all significant pairs. PCA was also used to generate a 3-dimensional plot of the top 3 variance contributors between the PPI-REE-pre and EoE cohorts by using the NL and PPI-REE-post cohorts as references. The paired t test was used to compare the treatment effect of paired samples before and after PPI. A 2-tailed P value of less than 0.05 was deemed statistically significant. For correlation analysis between eosinophil counts and gene dysregulation (EoE score [F59]), Spearman correlation was used to derive r and P values.

qPCR Analysis of DNA Expression

Figure 3B:
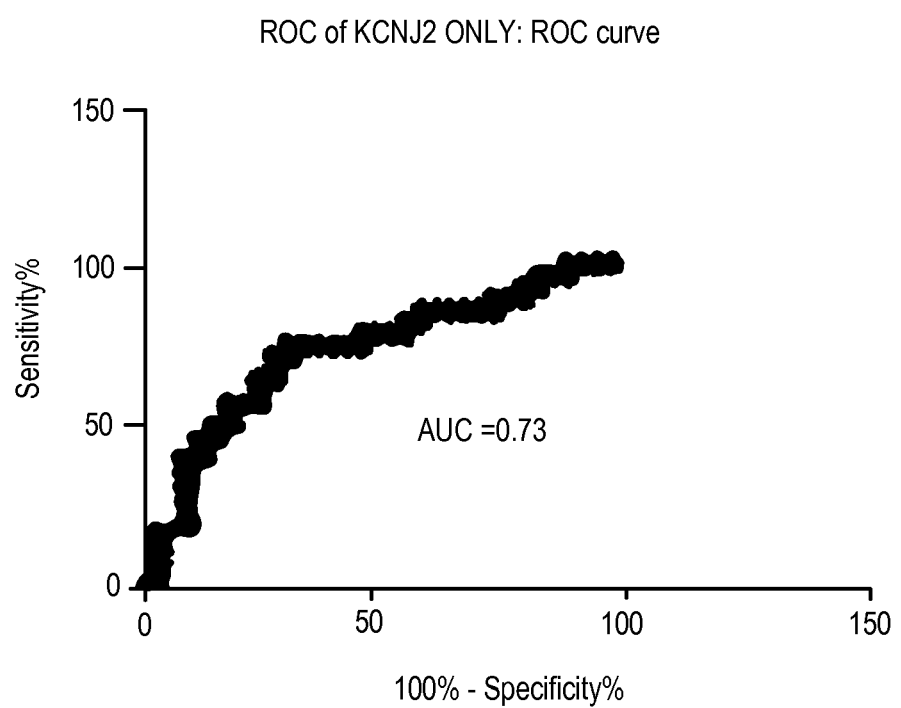

RNA was extracted from 60-80 μm tissue sections from formalin-fixed, paraffin-embedded (FFPE) blocks. RNA may also be extracted from frozen biopsy samples. qPCR was performed according to the manufacturer's instructions using an ABI 7900HT qPCR system. Briefly, 500-1000 ng RNA was reverse transcribed to cDNA and subjected to amplification by the system using KCNJ2-specific primers. FIG. 3 shows the results of a quantitative PCR-based (qPCR) analysis. Using qPCR, the AUC for discriminating EoE from PPI-REE-pre was 0.73 and the optimal threshold value (above which EoE is indicated) is 0.001128, where KCNJ2 gene expression is normalized to GADPH.

Confocal Microscopy Immunofluorescence Analysis of Protein Expression

Figure 4A:
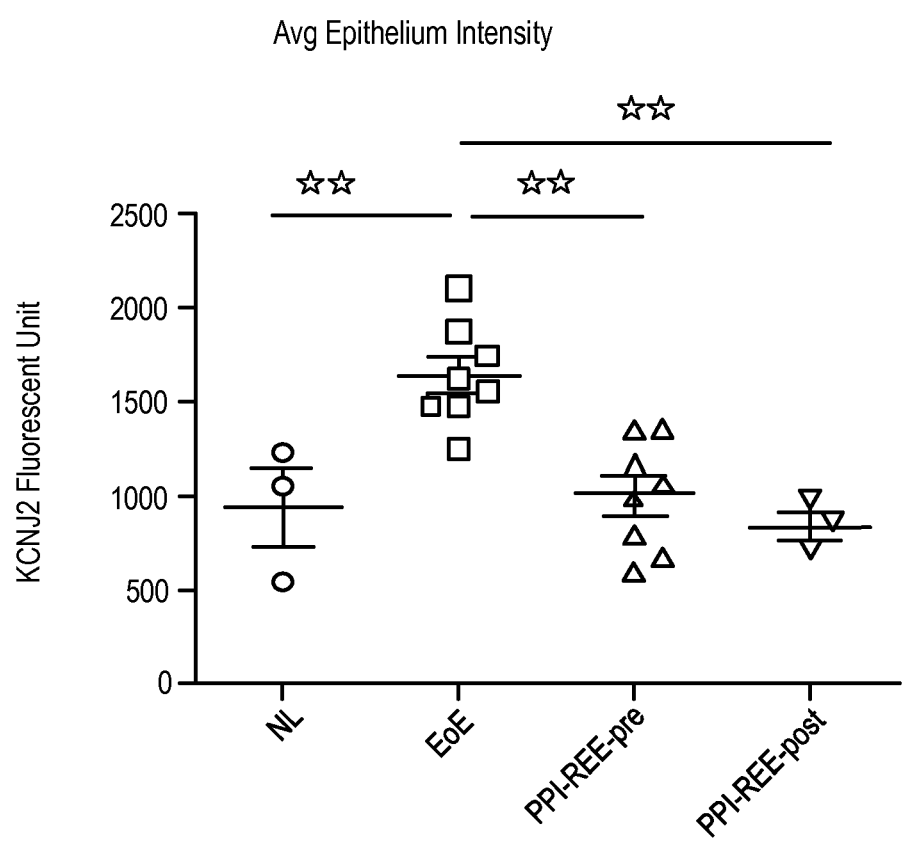
FIG. 4A-4B: A, Protein expression analysis of Kir2.1 using immunofluorescence quantitated by confocal microscopy, number of samples shown in parenthesis, NL (3), GERD (8), EoE (33,) PPI-REE-pre (8), PPI-REE-post (3), *$p<0.05$, $p<0.01$, *$p<0.001$; B, ROC of overall Epi avg:ROC curve showing AUC of 0.97.
Figure 4B:
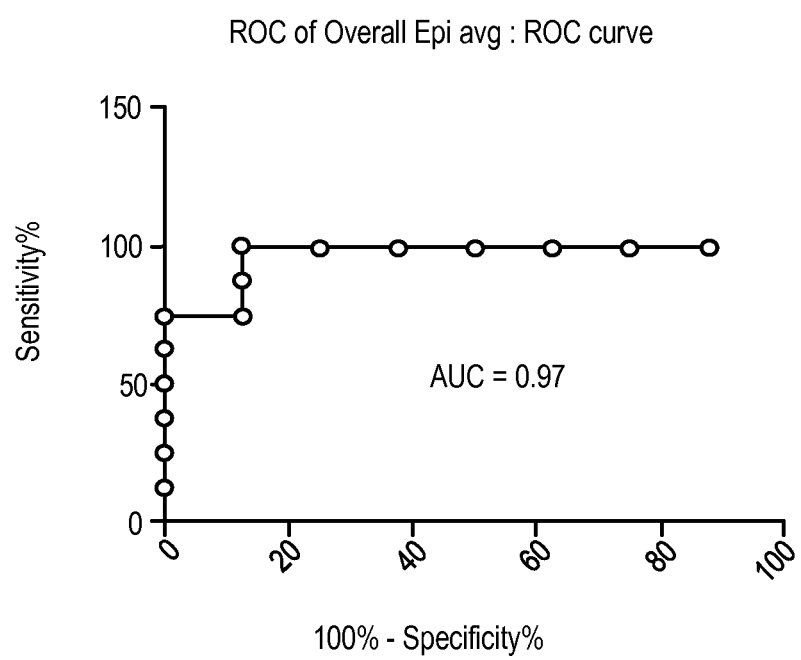

Biopsy sections are stained with a sequential immunofluorescence method (rabbit-anti-human KCNJ2, and Goat-anti-rabbit secondary conjugated to AF 488), and protein expression levels are quantitated from micrographs taken with a confocal microscope (Nikon Al Invert). The same sections are co-stained with a pan-epithelial marker, E-cadherin (CD324, mouse-anti-human) with donkey-anti-mouse AF 647 secondary antibody as epithelium identifier and overall signal normalizer. Digital quantification of the epithelium within the sections is performed by a workstation equipped with NIKON NIS Elements and Image J software. The computational algorithm involves computer-assisted fluorescent unit quantification, signal normalization to epithelium marker E-cadherin, and a receiver operating characteristic (ROC) binary classifier. FIG. 4 shows the results of this analysis. The AUC for this analysis was 0.97 and the optimal threshold value (above which EoE is indicated) is 1400 units, where the units are fluorescence units derived from the Nikon NIS elements software.

What is claimed is:

1. A method for diagnosing and treating eosinophilic esophagitis and proton pump inhibitor responsive esophageal eosinophilia (PPI-REE) in a patient in need of such diagnosis and treatment, the method comprising
    a. receiving or obtaining an esophageal biopsy sample from the patient;
    b. determining an expression level of a KCNJ2/Kir2.1 gene or gene product in the esophageal biopsy sample;
    c. determining whether the expression level of the KCNJ2/Kir2.1 gene or gene product in the esophageal biopsy sample is above or below a threshold level;
    d. diagnosing the patient as having eosinophilic esophagitis and administering a steroid to the patient having an expression level of the KCNJ2/Kir2.1 gene or gene product above the threshold level;
    e. diagnosing the patient as having PPI-REE and administering a proton pump inhibitor to the patient having an expression level of the KCNJ2/Kir2.1 gene or gene product below the threshold level.

2. The method of claim 1, wherein the method does not comprise a proton pump inhibitor (PPI) medication trial.

3. The method of claim 1, wherein the patient has not been previously treated with a proton pump inhibitor.

4. The method of claim 1, wherein the threshold level is relative to a reference expression level of the KCNJ2/Kir2.1 gene or gene product from normal esophageal tissue.

5. The method of claim 4, wherein normal esophageal tissue is defined as having each of the following characteristics: normal endoscopic results, normal pathology with 0 eosinophils/ high power field, and no known history of eosinophilic esophagitis in the patient from whom the sample was obtained.

6. The method of claim 4, wherein the reference is an average of a plurality of expression levels of the KCNJ2/Kir2.1 gene or gene product from a plurality of normal esophageal tissues.

7. The method of claim 1, comprising the step of determining the expression level of the KCNJ2/Kir2.1 gene, wherein said gene expression is determined using a quantitative PCR-based method.

8. The method of claim 7, wherein the expression level of the KCNJ2/Kir2.1gene is normalized.

9. The method of claim 8, wherein the threshold level is 2 or 3-fold greater than a reference expression level of the KCNJ2/Kir2.1 gene from normal esophageal tissue.

10. The method of claim 7, further comprising a step of extracting RNA from the esophageal biopsy sample.

11. The method of claim 10, further comprising a step of converting the RNA to cDNA.

12. The method of claim 11, further comprising a step of converting the cDNA into cRNA.

13. The method of claim 11, wherein the cDNA or cRNA is labeled with a detectable marker.

14. The method of claim 13, wherein the marker is biotin or a fluorescent molecule.

15. The method of claim 1, comprising the step of determining the expression level of the KCNJ2/Kir2.1 gene product, wherein said gene product expression is determined using an immunostaining-based method, an antibody-based method, or a method comprising mass spectrophotometry.

16. The method of claim 15, wherein the threshold level is 1.5-fold greater than a reference expression level of the KCNJ2/Kir2.1 gene product from normal esophageal tissue.

17. The method of claim 15, wherein the threshold level is given in normalized units.

18. The method of claim 1, wherein the method is performed in part using a computer program product, stored on a non-transitory computer readable medium, containing executable instructions that when executed cause a processor to perform operations comprising:

receiving the expression level of a KCNJ2/Kir2.1 gene or gene product in an esophageal biopsy sample obtained from a patient, and optionally, receiving a reference expression level of the KCNJ2/Kir2.1 gene or gene product from normal esophageal tissue;

receiving or calculating a threshold value;

comparing the KCNJ2/Kir2.1 gene or gene product expression level in the esophageal biopsy sample with the threshold value;

determining whether the KCNJ2/Kir2.1 gene or gene product expression level in the esophageal biopsy sample is above or below the threshold value;

outputting an indication of whether the KCNJ2/Kir2.1 gene or gene product expression level in the esophageal biopsy sample is above or below the threshold value.

19. The method of claim 18, wherein the indication is a patient-specific report.

20. The method of claim 18, wherein the report comprises a suggested diagnosis of eosinophilic esophagitis if the KCNJ2/Kir2.1 gene or gene product expression level in the esophageal biopsy sample is above the threshold value, or a suggested diagnosis of PPI-REE if the KCNJ2/Kir2.1 gene or gene product expression level in the esophageal biopsy sample is below the threshold value.

* * * * *